US012782017B2

(12) United States Patent
Stone

(10) Patent No.: US 12,782,017 B2
(45) Date of Patent: Nov. 3, 2026

(54) METHOD FOR SUPPLYING PRESSURIZED REFRIGERANT, AND PRESSURIZED REFRIGERANT TANK

(71) Applicant: Precision Impacts, LLC, Miamisburg, OH (US)

(72) Inventor: Adam C. Stone, Miamisburg, OH (US)

(73) Assignee: Precision Impacts LLC, Miamisburg, OH (US)

( * ) Notice: Subject to any disclaimer, the term of this patent is extended or adjusted under 35 U.S.C. 154(b) by 161 days.

(21) Appl. No.: 18/646,145

(22) Filed: Apr. 25, 2024

(65) Prior Publication Data

US 2024/0361055 A1 Oct. 31, 2024

Related U.S. Application Data

(60) Provisional application No. 63/462,792, filed on Apr. 28, 2023.

(51) Int. Cl.

| | |
|---|---|
| ***F25B 45/00*** | (2006.01) |
| ***F17C 5/02*** | (2006.01) |
| ***F25B 9/00*** | (2006.01) |
| *A61B 18/00* | (2006.01) |
| *A61B 18/20* | (2006.01) |

(52) U.S. Cl.

CPC ................ *F25B 45/00* (2013.01); *F17C 5/02* (2013.01); *F25B 9/002* (2013.01); *A61B 2018/00029* (2013.01); *A61B 18/20* (2013.01)

(58) Field of Classification Search

None

See application file for complete search history.

(56) References Cited

U.S. PATENT DOCUMENTS

| | | | |
|---|---|---|---|
| 6,234,352 | B1 | 5/2001 | Richard et al. |
| 7,028,488 | B2 | 4/2006 | Richard et al. |
| 8,287,579 | B2 | 10/2012 | Nimitz |
| 8,951,432 | B2 | 2/2015 | Boutier et al. |

(Continued)

FOREIGN PATENT DOCUMENTS

KR 102010580 B1 * 8/2019 ........... A61N 5/0616

OTHER PUBLICATIONS

"Solstice (R) Gas Blowing Agent | Technical Information", copyright 2022 Honeywell International Inc. retrieved from https://ess.honeywell.com/content/dam/advancedmaterials/en/documents/document-lists/blowing-agents/technical/TDS-Solstice-GBA-Feb2024.pdf.*

(Continued)

*Primary Examiner* — Jerry-Daryl Fletcher
*Assistant Examiner* — Daniel C Comings
(74) *Attorney, Agent, or Firm* — Lerner David LLP

(57) ABSTRACT

A method of filling a tank includes filling the tank with a predetermined amount of a liquid refrigerant under pressure and supplying an inert gas into the tank, such that, after the filling and supplying steps, the total pressure of the contents within the tank at an ambient temperature is at least 95% of the equilibrium vapor pressure of liquid R-134a at the ambient temperature. The total pressure of the contents within the tank may be in a range from 517.1 to 792.9 kPa when at a temperature of 21.1° C. The inert gas may be nitrogen, and the liquid refrigerant may be R-1234ze (E). The disclosed method may be utilized in connection with a tank for a laser treatment device for skin tissue.

20 Claims, 5 Drawing Sheets

(56) References Cited

U.S. PATENT DOCUMENTS

| | | | | |
|---|---|---|---|---|
| 11,072,733 | B2 | 7/2021 | Long | |
| 2020/0069955 | A1 * | 3/2020 | Collins .............. | A61B 18/1815 |

OTHER PUBLICATIONS

"Solstice (R) ze Refrgierant (HFO-1234ze): Ultra-Low GWP Hydrofluoroolefins (HFO) Alternative to Hydrofluorocarbons", copyright 2022 Honeywell International Inc. retrieved from https://prod-edam.honeywell.com/content/dam/honeywell-edam/pmt/oneam/en-us/refrigerants/documents/pmt-am-solstice-1234-ze-brochure.pdf.*

Anonymous, "candela cryogen—Parts4Laser", Nov. 28, 2022, Retrieved from the Internet: <URL:https://web.archive.org/web/20221128040608/ https:// parts41aser.com/product-tag/candela-cryogen/>.

Honeywell, "Honeywell-HF0-1234ze blowing agent", Honeywell fluoride products, Oct. 1, 2008, Retrieved from the Internet: <URL:https://www51.honeywell.com/sm/lgwp- fr/common/ . documents/FP>.

Honeywell, "How To Pressurize A 100 LB. (45.4 Kg) Cylinder Using Nitrogen", Jun. 1, 2020, Retrieved from the Internet: <URL:https://prod-edam.honeywell.com/content/dam/ honeywelledam/ pmt/oneam/en-us/blowing-agents/documents/pmt-amblowing- agents-pressurize1 OOlb-tech-guide.pdf?download=false>.

Honeywell, "Solstice Gas Blowing Agent", Mar. 27, 2023, Retrieved from the Internet: <URL:https://web.archive.org/web/20230327101159/ https:// advancedmaterials.honeywell.com/us/en/products/foam-blowingagents/ solstice-gas-blowing-agent#expand>.

International Search Report including Written Opinion from PCT/ US2024/026247, dated Aug. 21, 2024, pp. 1-17.

Honeywell, "Solstice GBA Conversion Manual" Feb. 2022. 46 pgs.

Honeywell, "Solstice Propellant, Technical Bulletin", Dec. 2017. 4 pgs.

* cited by examiner

METHOD FOR SUPPLYING PRESSURIZED REFRIGERANT, AND PRESSURIZED REFRIGERANT TANK

CROSS-REFERENCE TO RELATED APPLICATIONS

This application claims the benefit of the filing date of U.S. Provisional Patent Application No. 63/462,792 filed Apr. 28, 2023, the disclosure of which is hereby incorporated herein by reference.

BACKGROUND OF THE INVENTION

Refrigerants have been used for many applications for many years. Over time, however, environmental concerns have arisen about the impact on the environment due to the use of certain types of refrigerants, which led to restrictions on refrigerants with harmful side effects. For example, early refrigerants were chlorofluorocarbons (CFCs) or hydrochlorofluorocarbons (HCFCs), which were discovered to cause significant damage to the ozone layer (i.e., they had high ozone depletion potential (ODP) levels), and therefore such refrigerants started to be phased out in the mid-1980s in conjunction with the signing of the Montreal Protocol. In place of CFCs and HCFCs, hydrofluorocarbons (HFCs) were adopted because HFCs have zero ODP, and therefore pose no harm to the ozone layer. However, HFCs are greenhouse gasses, which have a high global warming potential (GWP). Therefore, HFCs are now also disfavored. More recently, there has been a movement toward the use of more environmentally-friendly refrigerants that have lower GWP values. Governmental regulations were adopted, which limit the quantities of high GWP refrigerants that can be imported and exported. For example, the European Union and other jurisdictions have introduced regulations limiting quantities of refrigerants having GWP values of 150 or higher.

A newer class of "fourth generation" refrigerants are hydrofluoroolefins (HFOs), which have low GWP values. An early HFO was R-1234yf, which was jointly developed by DuPont and Honeywell and is marketed under the name Opteon YF (by Chemours/DuPont) and Solstice YF (by Honeywell). R-1234yf has a GWP value of 4.

One application in which refrigerants are used includes tissue treatment devices utilizing lasers. For example, non-invasive laser treatment devices have been developed in which high-intensity electromagnetic energy is delivered to a location near or just under the surface of the skin to, for example, break up ink from tattoos in a tattoo removal procedure or to damage hair follicles in a hair removal procedure. However, such delivery of high-intensity energy can result in thermal injury (burns) to the skin, and associated pain. One way to reduce the risk of burns during laser treatment procedures is to spray a refrigerant (also known as a cryogen) on the surface of the skin in the target area for the laser treatment. This approach has the effect of cooling the skin in the treatment area and therefore, reducing pain from the procedure. The refrigerant sprayed by such treatment devices is often supplied from a tank, such as a compressed gas cylinder, detachably connected to the laser treatment machine. The detachable tank can be readily replaced when the refrigerant level runs low. The refrigerant is typically in a liquid form and is filled into the tank and put under pressure. During the laser treatment process, the pressurized refrigerant is dispensed onto the patient's skin and rapidly evaporates, resulting in a vapor that cools the skin to a substantially lower temperature than the ambient room temperature.

A popular refrigerant used with many laser treatment devices is R-134a (Preferred IUPAC Name: 1,1,1,2-Tetrafluoroethane). R-134a was beneficial for use in the laser treatment field in that it is categorized under the American Society of Heating, Refrigerating and Air-Conditioning Engineers (ASHRAE) Standard 34, and likewise under the International Organization for Standardization (ISO) Standard 817, as a safety group class A1 refrigerant, meaning that it is non-toxic (the 'A' designation) and that it is not flammable (the '1' designation), both of which are important considerations when a refrigerant is applied directly onto a person's skin and in proximity to laser energy. However, R-134a is an HFC that has a high GWP value of 1430. Thus, R-134a has recently been subject to strict regulations and limits in usage.

In connection with laser tissue treatment devices, alternative refrigerants that are more environmentally friendly have been explored for use in place of R-134a. For example, U.S. Pat. No. 8,287,579 to Nimitz ("Nimitz"), the content of which is incorporated herein by reference, discloses some possible refrigerants that could be utilized in that context. However, further improvement is desirable, particularly in achieving solutions that are as close as possible to "drop in" replacements, in which a pressurized tank containing the desired refrigerant can be readily connected to a laser treatment machine originally designed for use with a different refrigerant.

BRIEF SUMMARY OF THE INVENTION

Some aspects of the present invention provide methods of filling a gas tank with a liquid refrigerant. One method desirably includes filling the tank with the liquid refrigerant under pressure to a first filled state, and then supplying an inert gas into the tank to a second filled state. The order of the steps could be reversed, such that an inert gas is introduced into the tank before the liquid refrigerant. In the first filled state, the tank preferably contains no more than a predetermined limit of the liquid refrigerant, which results in the internal contents being at a first pressure at an ambient temperature. In the second filled state, the internal contents of the tank are preferably at a second pressure higher than the first pressure, when at the same ambient temperature as the first filled state.

In some of the above aspects of the invention, the second pressure is desirably at least 95% of the equilibrium vapor pressure of liquid R-134a at the same ambient temperature. For example, if the ambient temperature is about 75° F. (23.9° C.), and the equilibrium vapor pressure of liquid R-134a is about 93 psia (641.2 kPa) at that temperature, the second pressure would be about 88 psia (606.7 kPa). Or, if the ambient temperature is 70° F. (21.1° C.), at which temperature the equilibrium vapor pressure of liquid R-134a is 85.9 psia (592.3 kPa), the second pressure would be 81.6 psia (562.6 kPa). In other aspects of the invention, the second pressure may be in a range from 75 to 115 psia (517.1 to 792.9 kPa) when at the ambient temperature. Moreover, that ambient temperature may be 65-75° F. (18.33-23.89° C.). In accordance with other aspects of the invention, the liquid refrigerant may be R-1234ze(E), and, in accordance with some aspects of the invention, the inert gas may be nitrogen.

Another method of filling a gas tank with a liquid refrigerant in accordance with aspects of the present invention includes filling the tank with a predetermined amount of a liquid refrigerant under pressure and supplying an inert gas into the tank, such that, after the filling and supplying steps, the total pressure of the contents within the tank at an ambient temperature is at least 95% of the equilibrium vapor pressure of liquid R-134a at the ambient temperature.

In some of the above aspects of the invention, the predetermined amount of the liquid refrigerant may be less than or equal to a predetermined limit of the liquid refrigerant in the tank, where that predetermined limit is defined such that a volume of a liquid phase of the liquid refrigerant present in the tank would be less than an entire enclosed volume of the tank at any temperature up to an including 131° F. (55° C.). Thus, at an ambient room temperature of 70° F. (21.1° C.)), a vapor space within the tank may occupy about 10 percent of the enclosed volume of the tank when the predetermined amount of the liquid refrigerant in the tank is equal to the predetermined limit of the liquid refrigerant in the tank.

In some aspects of the invention, the filling step may be performed before the supplying step. In at least some aspects of the invention, the inert gas may be nitrogen.

In at least some aspects of the invention, the liquid refrigerant may be R-1234ze(E). In some aspects of the invention, the liquid refrigerant may have a global warming potential (GWP) value less than 150, and in further aspects of the invention the liquid refrigerant may have a GWP value less than 50 or less than 10. In other aspects of the invention, the liquid refrigerant may be one classified under ASHRAE 34 or ISO 817 as belonging to safety group class A1 or class A2L. In yet other aspects of the invention, the liquid refrigerant may have a boiling point less than 0° F. (−17.78° C.) at one atmosphere (101.325 kPa). In yet further aspects of the invention, the liquid refrigerant may have an equilibrium vapor pressure in a range from 60 to 90 psia (413.7 to 620.5 kPa) at 70° F. (21.1° C.).

In some aspects of the invention, after the filling and supplying steps, the total pressure within the tank at a temperature of 70° F. (21.1° C.) is at least 81.6 psia (562.6 kPa). In other aspects of the invention, after those steps, the total pressure within the tank at that temperature is less than 135 psia (930.8 kPa). In yet other aspects of the invention, after those steps, the total pressure within the tank at that temperature is in a range from 82 to 115 psia (565.4 to 792.9 kPa). In further aspects of the invention, after those steps, the total pressure within the tank at that temperature is in a range from 85 to 105 psia (586.1 to 724.0 kPa).

Yet another method of filling a gas tank with a liquid refrigerant in accordance with aspects of the present invention desirably includes filling the tank with a predetermined amount of R-1234ze(E) to a first filled state to achieve a first pressure at the first filled state and at an ambient temperature. The method preferably also includes supplying gaseous nitrogen into the tank to a second filled state to achieve a second pressure within the tank at the ambient temperature, where the second pressure is in a range from 75 to 115 psia (517.1 to 792.9 kPa) and is greater than the first pressure. In at least some aspects of the method, the predetermined amount of R-1234ze(E) is less than or equal to a predetermined limit of R-1234ze(E) in the tank, where that predetermined limit of R-1234ze(E) in the tank is defined such that a volume of a liquid phase of R-1234ze(E) present in the tank would be less than an entire enclosed volume of the tank at any temperature up to and including 131° F. (55° C.).

Yet another method of filling a gas tank with a liquid refrigerant in accordance with aspects of the present invention desirably includes filling the tank with a predetermined amount of a liquid refrigerant under pressure and supplying an inert gas into the tank, such that, after the filling and supplying steps, the total pressure of the contents within the tank is in a range from 75 to 115 psia (517.1 to 792.9 kPa) when at a temperature of 70° F. (21.1° C.). In at least some aspects of the method, the liquid refrigerant may be R-1234ze(E), and, in accordance with at least some aspects of the method, the inert gas may be nitrogen. In at least some other aspects of the method, the predetermined amount of the liquid refrigerant may be less than or equal to a predetermined limit of the liquid refrigerant in the tank, where that predetermined limit is defined such that a volume of a liquid phase of the liquid refrigerant present in the tank would be less than an entire enclosed volume of the tank at any temperature up to an including 131° F. (55° C.).

Another aspect of the present invention includes filled refrigerant tank including a liquid refrigerant and an inert gas disposed within the tank as discussed above. The contents of the tank are preferably pressurized to a pressure in a range from 75 to 115 psia (517.1 to 792.9 kPa) when they are at a temperature of 70° F. (21.1° C.). The tank preferably includes a nozzle through which the contents can be supplied into and dispensed from the tank. Moreover, the nozzle is preferably configured to detachably connect to a refrigerant supply connection of a laser treatment device for skin. The liquid refrigerant disposed within the tank is preferably R-1234ze(E), and the inert gas disposed therein may be nitrogen.

A filled refrigerant tank in accordance with aspects of the present invention includes liquid R-1234ze(E) and an inert gas disposed within the tank and pressurized to a pressure in a range from 75 to 115 psia (517.1 to 792.9 kPa) when at a temperature of 70° F. (21.1° C.). The tank preferably includes a nozzle through which the contents can be supplied into and dispensed from the tank. Moreover, the nozzle is preferably configured to detachably connect to a refrigerant supply connection of a laser treatment device for skin tissue. In at least some aspects of invention, the inert gas disposed in the tank may be nitrogen. In some other aspects of the invention, the enclosed volume of the tank may consist essentially of the liquid R-1234ze(E) and the inert gas.

A filled refrigerant tank in accordance with other aspects of the present invention includes liquid R-1234ze(E) and an inert gas disposed within the tank and pressurized to a pressure that is at least 95% of the equilibrium vapor pressure of liquid R-134a when at a temperature of 70° F. (21.1° C.). The tank preferably includes a nozzle through which the contents can be supplied into and dispensed from the tank. Moreover, the nozzle is preferably configured to detachably connect to a refrigerant supply connection of a laser treatment device for skin tissue. In at least some aspects of invention, the inert gas disposed in the tank may be nitrogen. In some other aspects of the invention, the enclosed volume of the tank may consist essentially of the liquid R-1234ze(E) and the inert gas.

In accordance with the above aspects, the invention may allow a more environmentally friendly refrigerant to achieve being an acceptable “drop in” replacement for a less environmentally friendly one in connection with a laser skin treatment device that was originally designed to use the less environmentally friendly refrigerant to cool a patient’s skin during a laser treatment procedure. Beneficially, the invention may lead to that result all while minimizing or even avoiding the need to reprogram the laser treatment device and/or the need for the user to operate the device any differently. The invention desirably also minimizes or eliminates any additional time that the device might otherwise require (or any errors that might occur) when handling the replacement refrigerant, such that the device can operate with the replacement refrigerant despite it having different properties than the original refrigerant. For example, the invention may desirably increase the pressure of the replacement refrigerant to at least approximately the pressure of the original refrigerant at the same ambient temperature. The invention desirably achieves that result without negatively impacting the properties of the replacement refrigerant and without exceeding the maximum permissible volume of the tank filled with the refrigerant.

DETAILED DESCRIPTION

Figure 1:
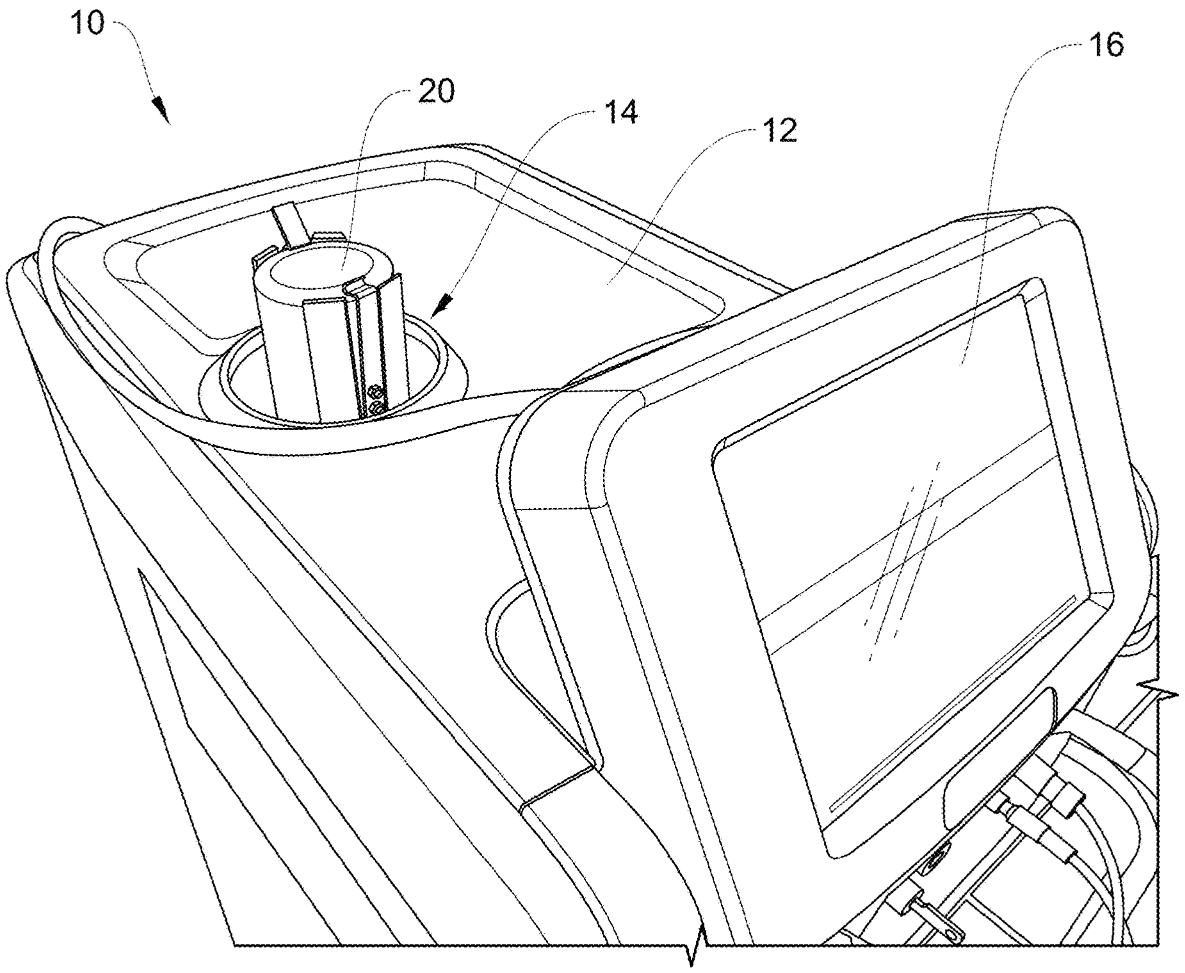
FIG. 1 is a photograph illustrating a cylindrical tank connected to a laser treatment device.

It is noted that the units "psia" and "psig" are referenced herein. Psia is a value representing "absolute pressure" in pounds per square inch, which is a measure of pressure relative to total vacuum. Psig, on the other hand, is "gauge pressure," meaning pressure in pounds per square inch relative to atmospheric pressure. Gauge pressure is commonly displayed by pressure gauges, but it is less universal in the sense that it varies based on changes in the atmospheric pressure, which in turn vary based on conditions such as altitude. Any values given in psia herein can be converted to psig by subtracting the local atmospheric pressure, which is about 14.7 psi at sea level. Conversely, any values given in psig herein can be converted to psia by adding the local atmospheric pressure.

Among the considerations in selecting desirable replacement refrigerants for tissue treatment devices is a low GWP value, particularly since the refrigerant evaporates into the atmosphere after it is sprayed onto a patient's skin. Other desirable characteristics include a boiling point that is as close as possible to the refrigerant being replaced. For example, where R-134a is the refrigerant being replaced, the substitute refrigerant will ideally have a boiling point relatively close to −15.34° F. (−26.3° C.) at one atmosphere (101.325 kPa). Other considerations include low flammability (particularly in connection with a laser application) and low toxicity (particularly in an application where the refrigerant is sprayed directly on a person's skin).

Other considerations in making an ideal "drop in" replacement include ensuring that the properties of the substitute refrigerant when dispensed are similar to the properties that the replaced refrigerant had when being dispensed. For example, having a similar dispensing pressure would be significant, so that the cooling gas maintains substantially the same effect when being ejected from the nozzle and contacting the patient's skin. Another consideration would be minimizing (or eliminating) the need to reprogram the laser treatment device that dispenses the refrigerant. Such reprogramming would involve logistical burdens in ensuring that all of the devices currently in service are updated, and would also require significant financial costs.

The following embodiment, which relates to implementation of the invention in connection with exemplary laser treatment devices marketed by Candela Corporation ("Candela") of Marlborough, Massachusetts, is illustrative of the principles of the present invention. Candela markets laser treatment devices under product names such as "Gentle Pro Series," "Vbeam® Perfecta," and "Vbeam® Prima" (hereinafter "Candela devices"). Such products include a handpiece that the operator positions near a target area of a patient's skin so that laser pulses can be applied to the target area. Such products may also be designed for use with cryogenic cooling by providing a nozzle on the handpiece so that pulses of refrigerant can be released towards the target area in conjunction with the laser pulses. That refrigerant is supplied from a standardized tank of pressurized liquid refrigerant that can be connected to the device and replaced as necessary.

FIG. 1 illustrates a cylindrical tank 20 of liquid refrigerant connected to a laser treatment device 10. Specifically, the top 12 of the laser treatment device 10 includes an opening 14 within which the tank 20 can be positioned. The device 10 includes a tank-receiving opening 14 positioned behind a display 16 (e.g., an LCD screen) that is located towards the front of the device 10. Although not shown in FIG. 1, the tank 20 includes an outlet through which the refrigerant is supplied. That outlet is positioned downwardly, where it is detachably connected to a refrigerant supply connection (not shown) positioned within the device 10.

Figure 2A:
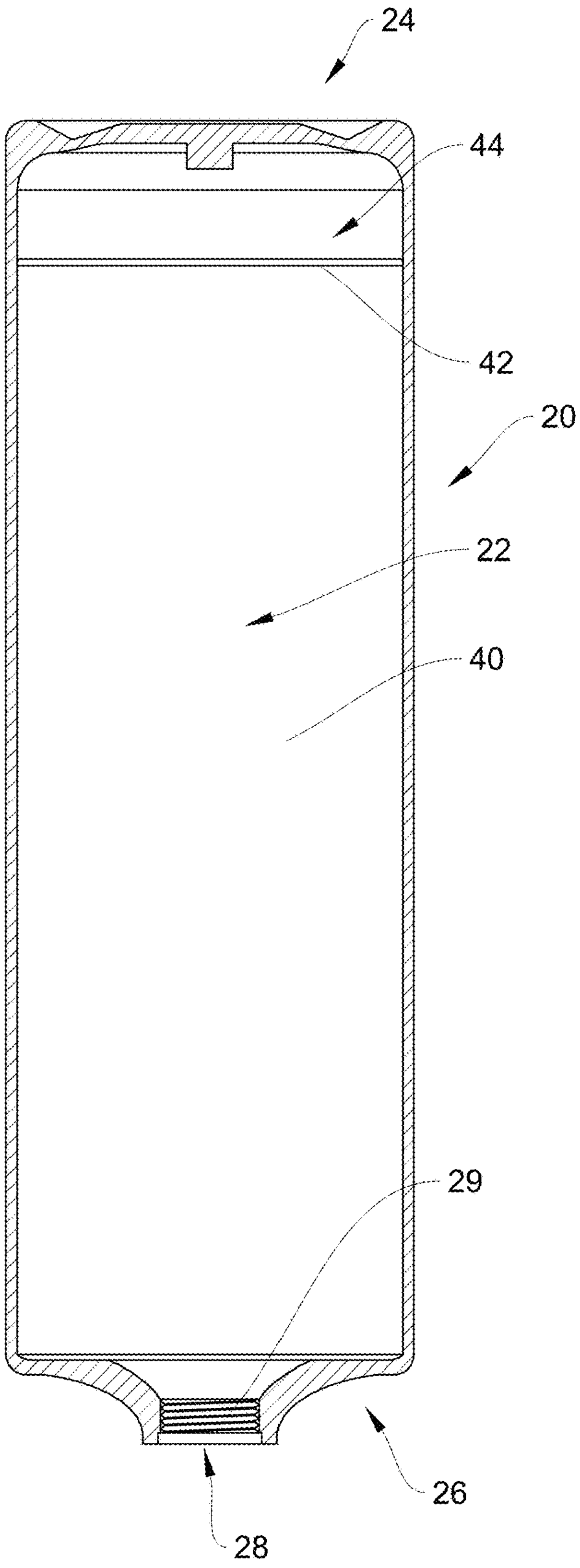
FIG. 2A is a cross-sectional view of a cylindrical tank for containing a refrigerant.

FIG. 2A illustrates a refrigerant-containing tank 20 positioned in the same vertical arrangement as when connected to the treatment device 10 in the manner shown in FIG. 1. The tank 20, when initially filled, includes liquid refrigerant 40 filled up to a certain level, generally a percentage less than 100% of the enclosed volume 22 of the tank 20. That filled level may be the maximally filled level for the given refrigerant at the ambient temperature, as discussed further below. FIG. 2A shows representative top surface line 42 of the liquid refrigerant, above which, near a top end 24 of the tank 20, is a vapor space 44 (also known as a "head space") containing gas in a gaseous state. At the other, bottom end 26 of the tank 20 is an opening 28 in which a valve 30 is positionable to fully enclose and seal the tank 20.

Figure 2B:
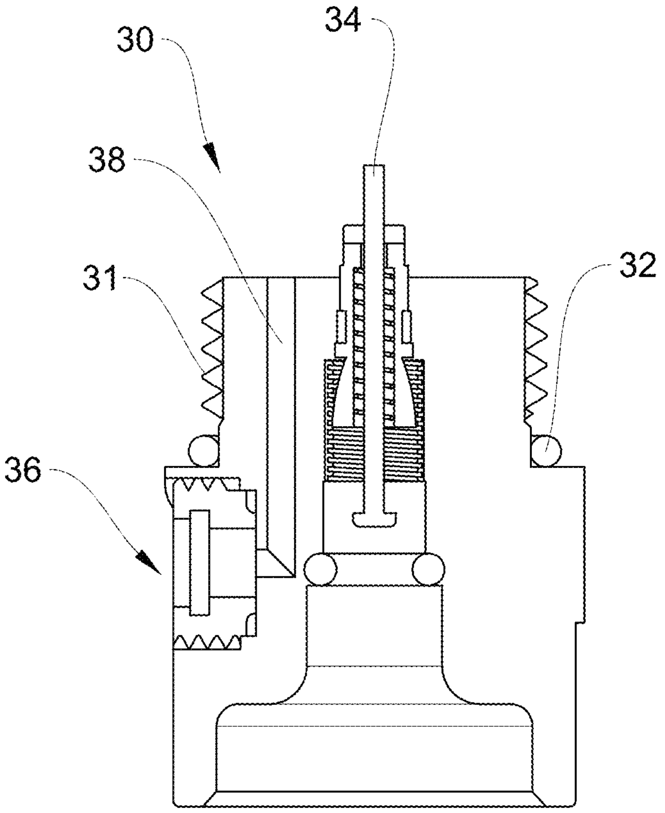
FIG. 2B is an enlarged cross-sectional view of a valve for the tank of FIG. 2A.

The opening 28 at the bottom end 26 of the tank 20 may include threads 29 for securing to threads 31 on the valve 30, as shown in FIG. 2B. An o-ring 32 may also be provided at an interface between the valve 30 and the perimeter of the opening 28 in order to create a fluid-tight seal. The valve 30 may be operated by depressing a valve stem 34 in order to open up fluid communication through the valve for dispensing the refrigerant 40 and/or for filling the tank 20. The valve 30 and the stem 34 may be a standardized design which is configured to operate with the refrigerant supply connection within the laser treatment device 10 such that the valve stem 34 is depressed when the valve 30 of the tank 20 is fully and properly seated against that connection. As also shown in FIG. 2B, the valve 30 may include a standard pressure relief device 36 for safety, which may operate by, for example, including a burst disc that is configured to rupture at a predefined excessive amount of pressure so that gases within the tank 20 can be vented via an associated passageway 38 communicating with the pressure relief device 36.

The Candela devices identified above were designed for use with tanks such as those illustrated in FIG. 2A and filled with liquid R-134a. Filled, in that context, means that such tanks 20 are not completely filled with liquid, but rather, for safety (and as required by law), the tank is "maximally filled" such that a certain minimum vapor space is provided in the tank, where the refrigerant exists in a gaseous state. The amount of vapor space as a percentage of the enclosed volume of the tank when the tank is maximally filled will vary depending on the contents of the tank and the temperature of those contents. One way of stating the maximally filled requirement is that the liquid phase of the refrigerant will not fill the entire enclosed volume of the tank at any temperature up to and including 131° F. (55° C.). Thus, at a temperature closer to ambient room temperature (e.g., 70° F. (21.1° C.)), the vapor space may occupy more like, for example, about 10 percent of the enclosed volume of the tank when the tank is maximally filled. When so filled with R-134a, the pressure of the contents of the tank are at an equilibrium vapor pressure of about 85.9 psia (592.3 kPa) at that ambient temperature. However, the Candela devices are designed to discharge the refrigerant at approximately 115 to 120 psig (about 130 to 135 psia), and such devices include internal heaters configured to heat up the connected tank until the pressure of its contents reaches that design pressure. Thus, when the pressurized tank maximally filled with liquid R.134a is heated to reach that pressure, the refrigerant will be dispensed with the originally-intended design values, in terms of properties such as mass flow rate and cooling effect. A preferred substitute refrigerant for R-134a in the above application would be R-1234ze(E) (Preferred IUPAC Name: trans-1,3,3,3-Tetrafluoroprop-1-ene), which was developed by Honeywell and is sold under the brand name SOLSTICE. That refrigerant in an environmentally friendly HFO that has a very low GWP value. Sources identify different GWP values for R-1234ze(E), with some identifying it as less than 10 and others stating that it is less than one. R-1234ze(E) is classified by ASHRAE and ISO as a safety group class A2L refrigerant. Again, the 'A' is a non-toxic designation, and the '2L' indicates low flammability. That is a higher flammability designation than for refrigerants considered non-flammable (with a '1' designation), but '2L' designated refrigerants are considered to have low flammability because their burning velocity is below 10 cm/s. R-1234ze(E) has a boiling point of −2.11° F. (−18.95° C.) at one atmosphere (101.325 kPa).

However, there are some unexpected challenges in implementing R-1234ze(E) as a refrigerant in connection with devices like the Candela devices identified above. For example, filling a tank to the same pressure as a tank maximally-filled with R-134a, as described above, would exceed the minimum allowable vapor space in the tank, since R-1234ze(E) has a lower equilibrium vapor pressure than R-134a within the range of typical ambient room temperatures. That is, at a temperature of 70° F. (21.1° C.), the equilibrium vapor pressure of R-1234ze(E) is about 63.2 psia (436 kPa), which is less than the 85.9 psia (592.3 kPa) of R-134a at the same temperature. As noted above, the Candela devices are configured to heat up the refrigerant tank until the pressure of its contents increases to the preset dispensing pressure. Therefore, in principle, tanks maximally-filled with R-1234ze(E) (with the minimum vapor space required for safety and/or by law) will be heated by the Candela devices until the pressurized refrigerant reaches the preset dispensing pressure, despite the pressure in such filled tanks starting out at a lower pressure than ones filled with R-134a. However, that can nevertheless lead to unanticipated problems, one of which is that it will take longer for pressure within the tank of R-1234ze(E) to reach the preset pressure. That can be significant to businesses using the laser treatment devices, as it could mean that fewer treatment procedures can be performed within a given time-period, due to the additional time required for the devices to reach operating state, and that would correlate with reduced revenue from the procedures. Moreover, the additional heating of the substitute refrigerant to reach the present temperature would result in the refrigerant being heated to a higher temperature than R-134a, which may negatively impact the cooling effect of the dispensed refrigerant vis-à-vis the originally-calibrated effect when R-134a was used. Another issue is that, if the additional heating up time takes too long or reaches too high a temperature, it can trigger programmed faults in the device that can result in the device not operating properly. Correction of that problem may require updating the programming of all devices currently in service, which would lead to the logistical and cost burdens noted above.

Figure 3A:
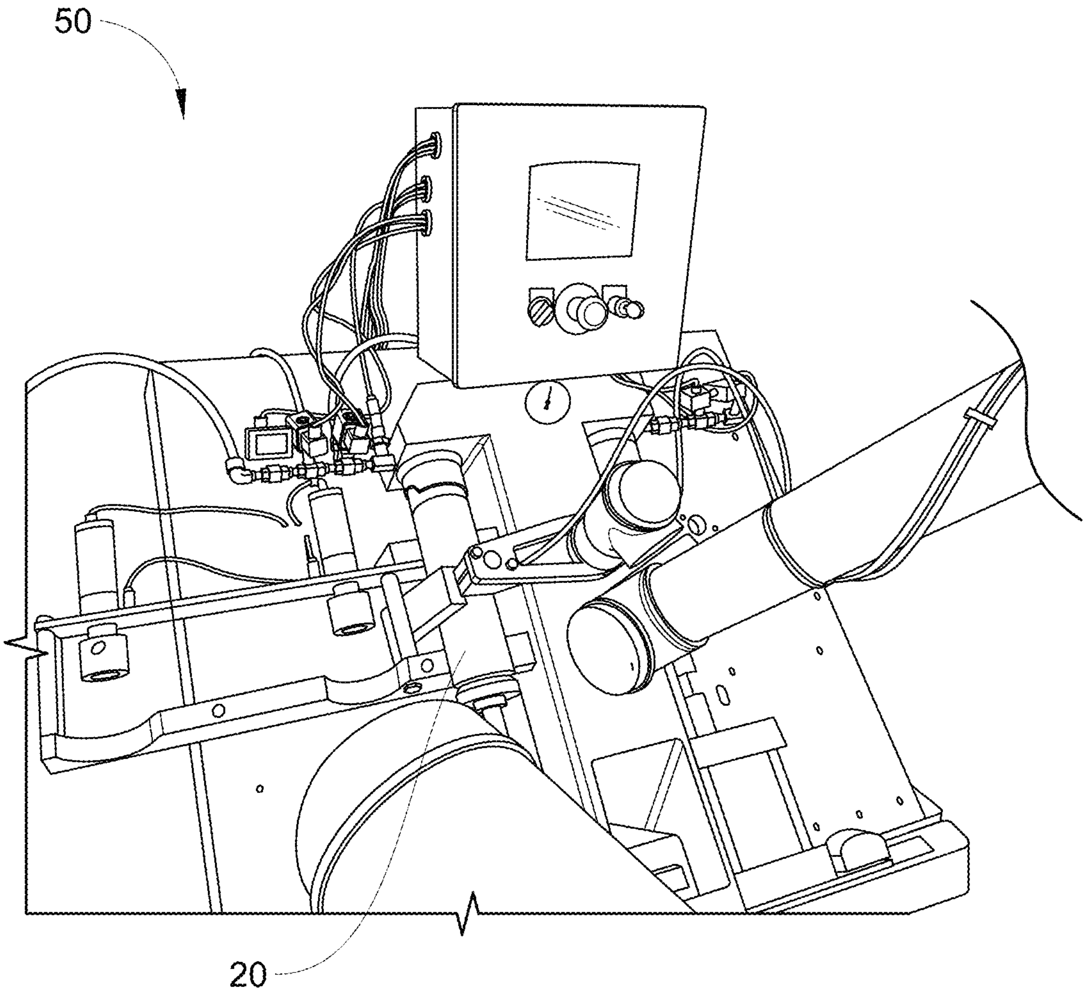
FIG. 3A is a photograph illustrating a cylindrical tank connected to a device for filling the tank with the refrigerant.
Figure 3B:
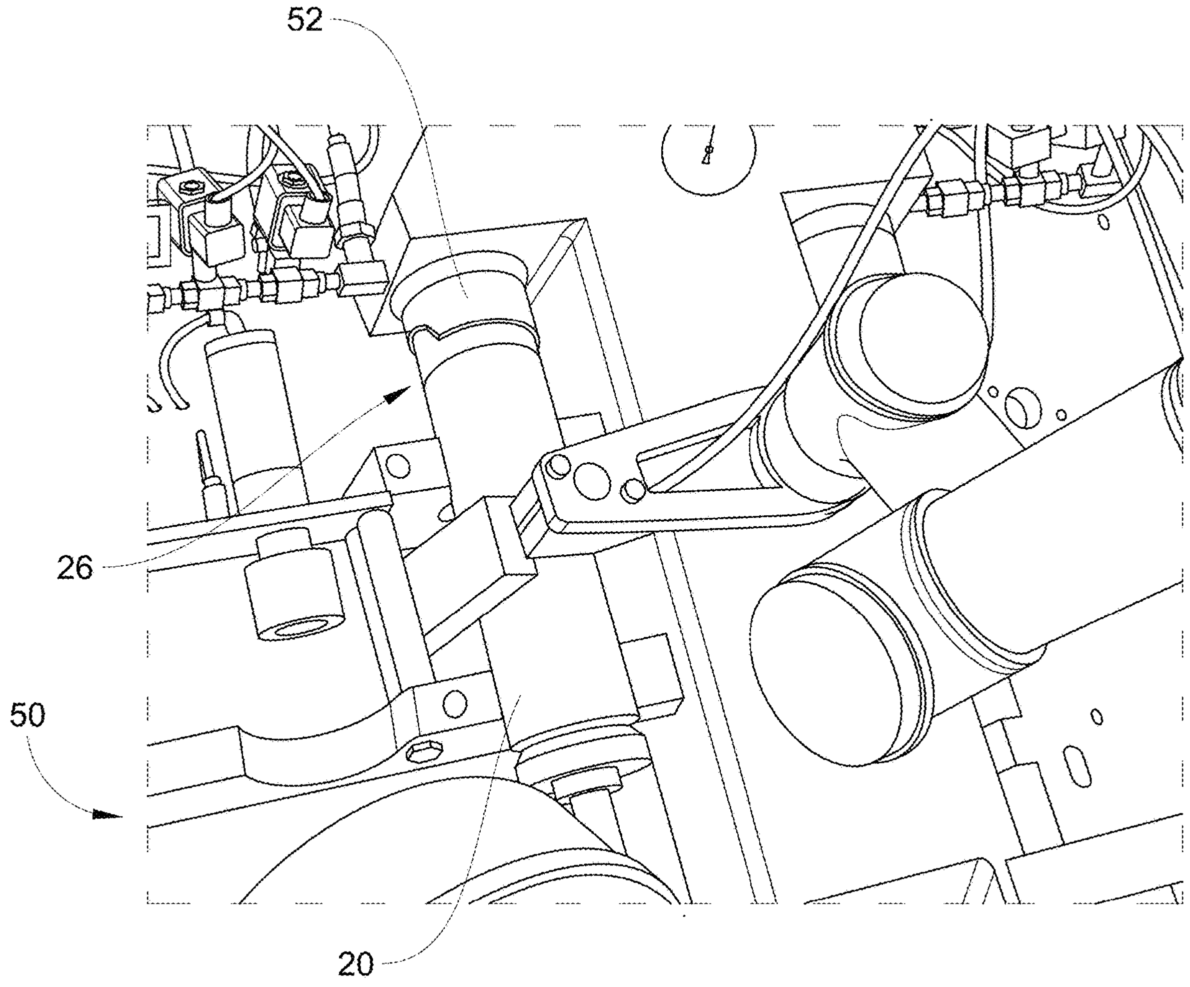
FIG. 3B is an enlarged view focusing on the tank as positioned in FIG. 3A.

Based on the present research and testing of alternative solutions to the above issues, a solution was developed that avoids and even improves upon at least some of such issues. Specifically, the invention includes a process of increasing the pressure of the R-1234ze(E) refrigerant contained within a tank without sacrificing the minimum vapor space within the tank. That process includes filling a tank with approximately the maximum amount of liquid R-1234ze(E) (while maintaining the minimum vapor space). Then, an inert gas is added to the tank to increase the pressure to a target higher pressure. The inert gas is preferably nitrogen, although other inert gases could be used. Air and pure oxygen should be avoided, however, as the presence of oxygen could detrimentally increase flammability. FIGS. 3A and 3B illustrate a tank 20 connected to a filling apparatus 50, which includes a connection 52 to the valve 30 at the bottom end 26 of the tank 20. That connection 52 may be structured to depress the valve stem 34, similarly to the connection within the laser treatment device 10 mentioned above, so that the gases (i.e., the liquid refrigerant and the gaseous inert gas) can be supplied into the tank 20.

The target higher pressure level reached by increasing the pressure with an inert gas, as discussed above, could be approximately the pressure of a maximally-filled R-134a tank at the same temperature. In another example, the target pressure could be even higher, which would reduce the heat up time when used in the Candela devices (and other laser treatment devices) and would therefore lead to benefits to the businesses owning such devices. Such target pressure should be below the preset dispensing pressure, since the devices may only be configured to heat up the refrigerant to increase the pressure to the dispensing pressure, rather than cooling down the refrigerant to decrease the pressure. Moreover, given possible variations in room temperatures where the devices in service are located, the target pressure should be sufficiently below the preset dispensing pressure such that the pressures within the tank remain below that dispensing pressure in a variety of reasonably anticipated room temperatures. Furthermore, it may be desirable to further limit the target pressure so as to avoid triggering any pre-programmed faults in the devices, such as programming that may trigger an error and/or prevents the heat up process from progressing if the initial (pre-heating) pressure is higher than some setpoint. Therefore, one desired range of target pressures (when at an ambient temperature of 70° F. (21.1° C.)) is from 75 to 115 psia (517.1 to 792.9 kPa). Other ranges are also desirable. For example, the range of internal pressures at ambient temperature may be 80-115 psia (551.6-792.9 kPa), 80-110 psia (551.6-758.4 kPa), 85-110 psia (586.1-758.4 kPa), 90-110 psia (620.6-758.4 kPa), 95-110 psia (655.0-758.4 kPa), 100-110 psia (689.5-758.4 kPa), 85-105 psia (586.1-724.0 kPa), 90-105 psia (620.6-724.0 kPa), 95-105 psia (655.0-724.0 kPa), 90-100 psia (620.6-689.5 kPa), 95-100 psia (655.0-689.5 kPa), and 82 to 115 psia (565.4 to 792.9 kPa). In other examples, the range of internal pressures may be about one of those ranges identified above, where "about" means that the identified lower bound and/or the identified upper bound can be varied by up to 1 psia (6.9 kPa).

By utilizing the above method, the pressure of the tank containing R-1234ze(E) will desirably be increased to the target pressure without impacting the properties of the refrigerant, due to the use of an inert gas. Moreover, when the tank is positioned within the device in the vertical orientation (shown in FIG. 2A), the gaseous nitrogen will be located within the vapor space 44 near the top end 24 of the tank 20, while the liquid R-1234ze(E) refrigerant will be positioned below the top surface line 42 and resting, due to gravity, against the valve 30. Thus, during dispensing of the refrigerant, only the R-1234ze(E) refrigerant will be dispensed while the inert gas remains in the vapor space 44 near the top end 24 of the tank 20.

Although the above-described method involved adding the liquid refrigerant to the tank before the gaseous inert gas, such as nitrogen, is added, the method could also encompass performing those steps in the reverse order. For example, if it were known in advance what amount of refrigerant would be added to maximally fill the tank, as well as what amount of the inert gas would be added to bring the pressure in the tank up to the target pressure, then such quantities of liquid refrigerant and inert gas could be added in the reverse order.

The above-described implementation of the present invention can be implemented in a variety of possible variations, each of which is contemplated as being encompassed by an independent aspect of the present invention. For example, alternative refrigerants may be used as the substitute refrigerant, and the above methodology may be used to increase the pressure of the substitute refrigerant by adding an inert gas (e.g., nitrogen) to the tank until the substitute refrigerant is at a target pressure that is at least at approximately (e.g., 95% of) the pressure of the refrigerant being replaced (e.g., the equilibrium vapor pressure of R-134a). Such target pressure is also desirably below the preset dispensing pressure of a device to which it is to be connected (at a reasonably broad range of anticipated room temperatures) and/or below a preset pressure that (at such reasonably broad range of anticipated room temperatures) would cause a fault in the device.

Possible alternative refrigerants that could be used as a substitute refrigerant in accordance with the above include refrigerants classified by ASHRAE and ISO as safety group class A1 refrigerants and/or class A2L refrigerants. Preferably, the selected alternative refrigerants have a relatively low GWP value. For example, selected alternative refrigerants may have a GWP value under 150. Even more preferably, such alternative refrigerants may have a GWP value under 50. Even more preferably, such alternative refrigerants may have a GWP value under 10. As further examples, other HFO refrigerants could be selected. In yet other examples, any of the refrigerants identified in the Nimitz patent could be used.

Another implementation of the invention disclosed herein is a filled refrigerant tank containing a substitute refrigerant for R-134a and an inert gas. Both the substitute refrigerant and the inert gas disposed within the tank may be pressurized to a pressure that is at least 95% of the equilibrium vapor pressure of liquid R-134a when at an ambient temperature. For example, at an ambient temperature of 70° F.

(21.1° C.), the equilibrium vapor pressure of liquid R-134a is 85.9 psia (592.3 kPa), and therefore 95% of that pressure would be 81.6 psia (562.6 kPa). In another implementation, both the substitute refrigerant and the inert gas disposed within the tank may be pressurized to a pressure in a range from 75 to 115 psia (517.1 to 792.9 kPa) when at a temperature of 70° F. (21.1° C.). As noted above, the inert gas utilized in the filled refrigerant tank may be nitrogen.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of filling a tank for a laser treatment device, comprising:

filling a tank for a laser treatment device for skin tissue with a predetermined amount of a liquid refrigerant under pressure, the tank having a nozzle configured to detachably connect to a refrigerant supply connection of the laser treatment device; and supplying an inert gas into the tank;

wherein, after the filling and supplying steps, when the tank is at an ambient temperature, a total pressure within the tank would be at least 95% of the equilibrium vapor pressure of liquid R-134a at the ambient temperature.

2. The method of claim 1, wherein the liquid refrigerant is R-1234ze (E).

3. The method of claim 1, wherein the inert gas is nitrogen.

4. The method of claim 1, wherein the filling step is performed before the supplying step.

5. The method of claim 1, wherein the predetermined amount of the liquid refrigerant is less than or equal to a predetermined limit of the liquid refrigerant in the tank, the predetermined limit being defined such that a volume of a liquid phase of the liquid refrigerant present in the tank would be less than an entire enclosed volume of the tank at any temperature up to and including 131° F.

6. The method of claim 1, wherein the liquid refrigerant has a GWP (global warming potential) value less than 150.

7. The method of claim 6, wherein the liquid refrigerant has a GWP value less than 50.

8. The method of claim 6, wherein the liquid refrigerant has a GWP value less than 10.

9. The method of claim 1, wherein the liquid refrigerant is classified under ASHRAE 34 or ISO 817 as belonging to safety group class A1 or class A2L.

10. The method of claim 1, wherein the liquid refrigerant has a boiling point less than 0° F. at one atmosphere.

11. The method of claim 1, wherein the liquid refrigerant has an equilibrium vapor pressure of in a range from 60 to 90 psia at 70° F.

12. The method of claim 1, wherein, after the filling and supplying steps, the total pressure within the tank at a temperature of 70° F. is at least 81.6 psia.

13. The method of claim 12, wherein, after the filling and supplying steps, the total pressure within the tank at the temperature of 70° F. is less than 135 psia.

14. The method of claim 13, wherein, after the filling and supplying steps, the total pressure within the tank at the temperature of 70° F. is in a range from 82 to 115 psia.

15. A method of filling a tank for a laser treatment device, comprising:

filling a tank for a laser treatment device for skin tissue with a predetermined amount of R-1234ze (E) to a first filled state to achieve a first pressure at the first filled state and at an ambient temperature, the tank having a nozzle configured to detachably connect to a refrigerant supply connection of the laser treatment device; and supplying gaseous nitrogen into the tank to a second filled state to achieve a second pressure within the tank at the ambient temperature, where the second pressure is in a range from 80 to 110 psia and is greater than the first pressure.

16. The method of claim 15, wherein the predetermined amount of R-1234ze (E) is less than or equal to a predetermined limit of R-1234ze (E) in the tank, the predetermined limit of R-1234ze (E) in the tank being defined such that a volume of a liquid phase of R-1234ze (E) present in the tank would be less than an entire enclosed volume of the tank at any temperature up to and including 131° F.

17. A method of filling a tank for a laser treatment device, comprising:

filling a tank for a laser treatment device for skin tissue with a predetermined amount of a liquid refrigerant under pressure, the tank having a nozzle configured to detachably connect to a refrigerant supply connection of the laser treatment device; and supplying an inert gas into the tank;

wherein, after the filling and supplying steps, when the tank is at a temperature of 70° F., a total pressure within the tank would be in a range from 80 to 110 psia.

18. The method of claim 17, wherein the liquid refrigerant is R-1234ze (E).

19. The method of claim 17, wherein the inert gas is nitrogen.

20. The method of claim 17, wherein the predetermined amount of the liquid refrigerant is less than or equal to a predetermined limit of the liquid refrigerant in the tank, the predetermined limit being defined such that a volume of a liquid phase of the liquid refrigerant present in the tank would be less than an entire enclosed volume of the tank at any temperature up to and including 131° F.

* * * * *